(12) United States Patent
Deighan et al.

(10) Patent No.: US 8,684,979 B2
(45) Date of Patent: Apr. 1, 2014

(54) DISCRIMINATING FLUID CONNECTION SYSTEM

(75) Inventors: Ciara Deighan, Kinnitty (IE); Paul J. Daly, Tullamore (IE); Alan Fitzgerald, Edgeworthstown (IE); David Rork Swisher, St. Charles, MO (US)

(73) Assignee: Covidien LP, Mansfield, MA (US)

( * ) Notice: Subject to any disclaimer, the term of this patent is extended or adjusted under 35 U.S.C. 154(b) by 84 days.

(21) Appl. No.: 12/774,839

(22) Filed: May 6, 2010

(65) Prior Publication Data

US 2010/0283238 A1 Nov. 11, 2010

Related U.S. Application Data

(60) Provisional application No. 61/177,024, filed on May 11, 2009.

(51) Int. Cl.
*A61M 5/31* (2006.01)

(52) U.S. Cl.
USPC .......... 604/241; 604/533; 285/332.1; 285/399

(58) Field of Classification Search
USPC ............... 285/125.1, 129.1, 331, 332, 332.1, 285/332.2, 332.3, 123.1, 123.3, 123.15, 285/123.16, 399; 251/142, 148; 604/533, 604/537, 905, 241, 240, 284, 248
See application file for complete search history.

(56) References Cited

U.S. PATENT DOCUMENTS

| | | | |
|---|---|---|---|
| 1,954,454 A * | 4/1934 | McFarland | 277/591 |
| 3,752,510 A | 8/1973 | Windischman et al. | |
| 4,211,439 A | 7/1980 | Moldestad | |
| 4,607,868 A | 8/1986 | Harvey et al. | |
| 4,617,012 A | 10/1986 | Vaillancourt | |
| 4,619,640 A | 10/1986 | Potolsky et al. | |
| 5,017,188 A | 5/1991 | Marten et al. | |
| 5,032,116 A | 7/1991 | Peterson et al. | |
| 5,057,093 A | 10/1991 | Clegg et al. | |
| 5,242,425 A | 9/1993 | White et al. | |
| 5,267,983 A | 12/1993 | Oilschlager et al. | |
| 5,355,876 A * | 10/1994 | Brodsky et al. | 128/202.27 |
| 5,395,348 A | 3/1995 | Ryan | |
| 5,725,511 A | 3/1998 | Urrutia | |

(Continued)

FOREIGN PATENT DOCUMENTS

| | | |
|---|---|---|
| CA | 2741525 A1 | 3/2008 |
| EP | 2269685 A2 | 1/2011 |

(Continued)

OTHER PUBLICATIONS

Exam Report issued Oct. 29, 2012 in related Canadian application No. 2703429, 3 pgs.

(Continued)

*Primary Examiner* — James Hewitt
*Assistant Examiner* — Jay R Ripley

(57) ABSTRACT

A discriminating connector system for medical use. The connector system includes a male connector and a female connector. A standoff of the male connector forms a sealed, fluid connection with a receptacle of the female connector for fluid flow between conduits connected to the male and female connectors. The construction of the connector system prevents connection of either the male or female connector to other non-conforming connectors or syringes commonly found in medical environments, such as male and female luer-lock connectors and syringes.

9 Claims, 25 Drawing Sheets

(56) References Cited

U.S. PATENT DOCUMENTS

| | | | |
|---|---|---|---|
| 5,925,028 A | 7/1999 | Delvigo | |
| 6,402,207 B1 | 6/2002 | Segal et al. | |
| 6,464,686 B1 | 10/2002 | O'Hara et al. | |
| 6,467,651 B1 * | 10/2002 | Muderlak et al. | 222/52 |
| 6,612,624 B1 | 9/2003 | Segal et al. | |
| 6,673,059 B2 | 1/2004 | Guala | |
| 6,745,998 B2 * | 6/2004 | Doyle | 251/149.6 |
| 6,874,522 B2 | 4/2005 | Anderson et al. | |
| 6,979,322 B2 | 12/2005 | Chu et al. | |
| 7,140,592 B2 * | 11/2006 | Phillips | 251/149.6 |
| 7,240,926 B2 | 7/2007 | Dalle et al. | |
| 7,611,317 B2 * | 11/2009 | Muderlak et al. | 411/522 |
| 7,914,519 B2 | 3/2011 | Moran et al. | |
| 8,066,688 B2 * | 11/2011 | Zinger et al. | 604/411 |
| 8,257,286 B2 | 9/2012 | Meyer et al. | |
| 2002/0128607 A1 | 9/2002 | Haury et al. | |
| 2004/0034324 A1 | 2/2004 | Seese et al. | |
| 2005/0090805 A1 * | 4/2005 | Shaw et al. | 604/523 |
| 2006/0108555 A1 * | 5/2006 | Kiehne | 251/149.7 |
| 2006/0142735 A1 * | 6/2006 | Whitley | 604/537 |
| 2007/0060898 A1 | 3/2007 | Shaughnessy et al. | |
| 2008/0103486 A1 | 5/2008 | Owens | |
| 2008/0140020 A1 | 6/2008 | Shirley | |
| 2008/0140055 A1 | 6/2008 | Shirley | |
| 2008/0318456 A1 * | 12/2008 | Yow et al. | 439/157 |
| 2009/0099552 A1 | 4/2009 | Levy et al. | |
| 2009/0326481 A1 | 12/2009 | Swisher et al. | |

FOREIGN PATENT DOCUMENTS

| | | |
|---|---|---|
| JP | 63111146 U | 7/1988 |
| JP | 2001299906 A | 10/2001 |
| JP | 2001299936 A | 10/2001 |
| JP | 2002028224 A | 1/2002 |
| JP | 2002078797 A | 3/2002 |
| WO | 2007030403 A2 | 3/2007 |
| WO | 2008049568 A1 | 5/2008 |

OTHER PUBLICATIONS

Exam Report dated Jul. 12, 2013 regarding corresponding Canadian Patent Application No. 2,703,429, 3 pages.

* cited by examiner

DISCRIMINATING FLUID CONNECTION SYSTEM

CROSS REFERENCE TO RELATED APPLICATION

This application claims the benefit of U.S. Ser. No. 61/177,024, filed May 11, 2009, which is incorporated herein by reference in its entirety.

FIELD OF INVENTION

The present invention generally relates to fluid connection systems and more particularly to a discriminating fluid connection system.

BACKGROUND OF THE INVENTION

Tubing and catheter misconnections are a serious problem in hospitals. One type of tube and catheter misconnection error involves enteral feeding tubes and intravenous catheters. Enteral feeding tubes are used to administer liquid nutritional solutions and medications directly to a patient's gastrointestinal system. In contrast, intravenous catheters are used to administer medications and the like directly to a patient's vascular system. Patients may be harmed if feeding solutions are administered intravenously and vice versa. Errors such as this occur because of medical professionals using similar or identical tubing for different purposes. For example, luer tips, including luer-lock components, contribute to many of these errors because they enable functionally dissimilar tubes or catheters to be connected. In other words, a luer tip may be inserted improperly into a connector or adaptor of a feeding tube, with potentially harmful results.

SUMMARY OF THE INVENTION

In one aspect of the present invention, a connection system for forming a sealed fluid connection generally comprises a first connector that comprises a floor and an annular wall extending from the floor. The first connector also comprises a standoff projecting from the floor within the annular wall and disposed for blocking nonconforming connectors from entering into fluid connection with the annular wall of the first connector. The first connector also comprises at least one opening in at least one of the standoff and the floor. The system also comprises a second connector that comprises a floor and an annular wall adapted to form a sealed fit connection with the annular wall of the first connector to provide a fluid tight passage between the first and second connectors. The second connector also comprises a receptacle projecting from the floor of the second connector to receive the standoff of the first connector and to permit the annular wall of the first connector to come into sealing engagement with the annular wall of the second connector to form the fluid tight passage. At least one opening in the floor of the second connector is disposed radially outward from the receptacle.

In another aspect of the present invention, a discriminating connector for use in inhibiting incorrect fluid connections in a medical environment generally comprises a floor and an annular wall extending from the floor. The connector also comprises a discriminating structure projecting from the floor within the annular wall and disposed for blocking nonconforming connectors from entering into fluid connection with the annular wall of the connector. The connector also comprises at least one opening in at least one of the discriminating structure and the floor to permit passage of fluid through the connector around the discriminating structure.

In yet another aspect of the present invention, a connection system for forming a sealed connection between a first conduit and a second conduit generally comprises a first connector adapted for connection to the first conduit. The first connector defines a passage having an axis and a first surface having a plane with a first angular orientation with respect to said axis. The first surface comprises one or more subsurfaces, each subsurface having a plane with a different angular orientation to said axis than the first angular orientation. The system also comprises a tip connector continuous with the second conduit and comprising a second surface that is shaped to be complementary to the first surface.

In yet another aspect of the present invention, a connector system for forming a sealed connection between fluid delivery lines. The connector system comprises a first connector having a longitudinal axis and a connection surface having a fluid opening therein. The connection surface is arranged at an angle to the longitudinal axis of the first connector. The system also comprises a second connector having a longitudinal axis and a connection surface having a fluid opening therein. The connection surface of the second connector is arranged at an angle to the longitudinal axis of the second connector. The connection surface of the second connector is arranged to be complementary to the connection surface of the first connector. Upon connection of the first connector with the second connector, the connection surfaces are in face to face position with the fluid openings of the first and second connectors in general alignment for passage of fluid through the fluid openings.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
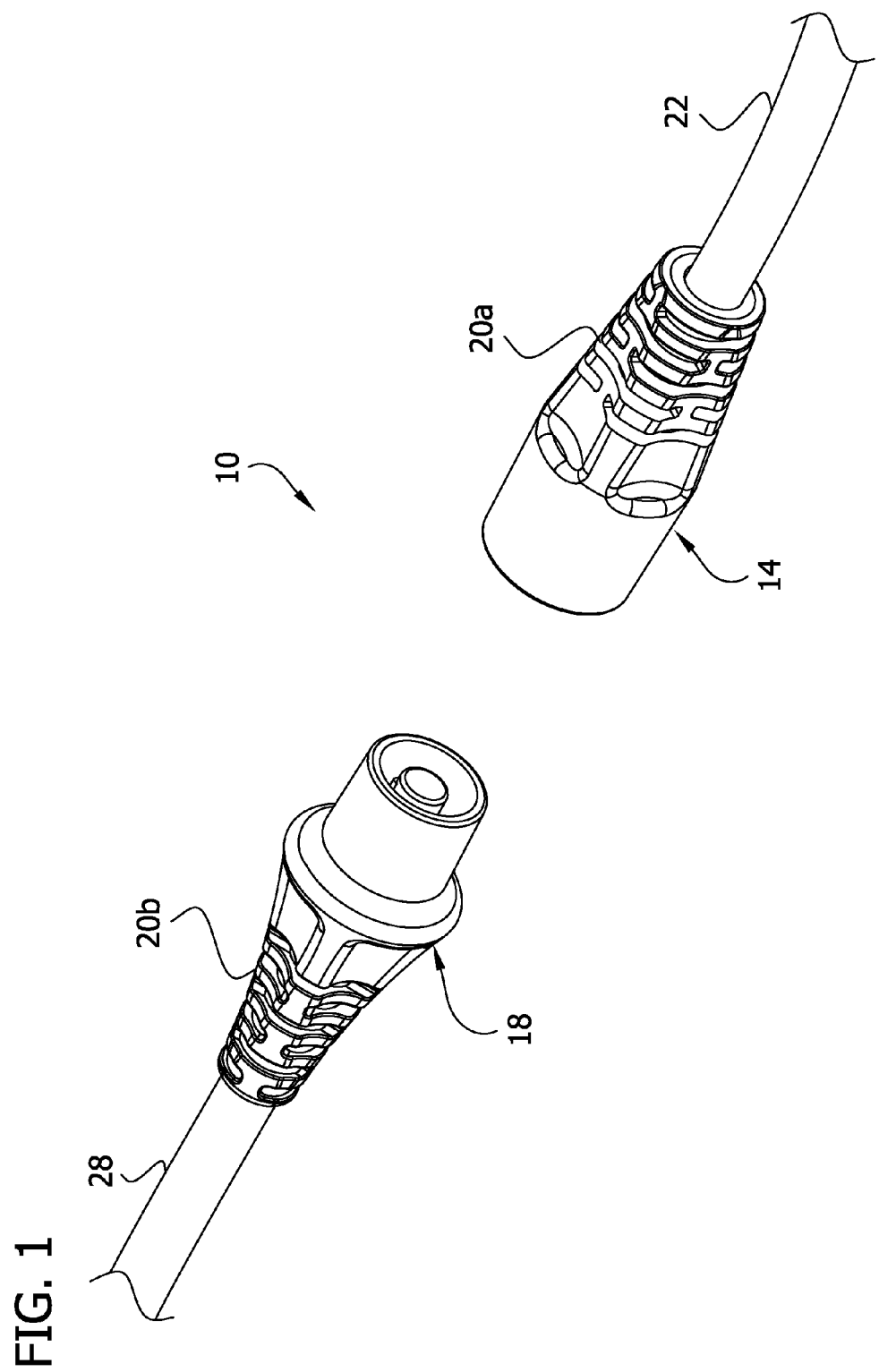
FIG. 1 is a perspective showing a discriminating connection system of the invention in an unlocked configuration.
Figure 2:
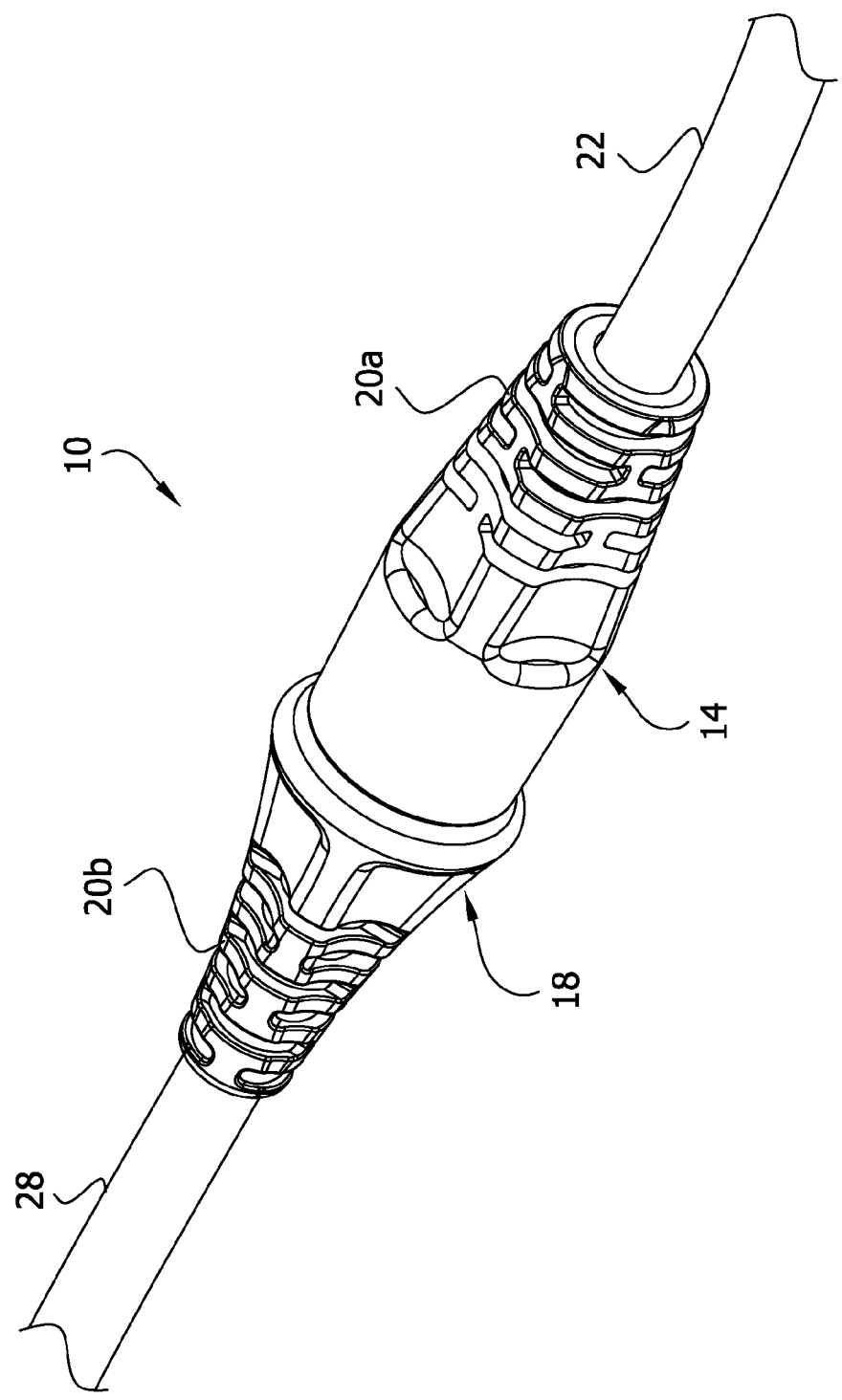
FIG. 2 is a perspective showing the discriminating connection system of FIG. 1 in a locked configuration.
Figure 3:
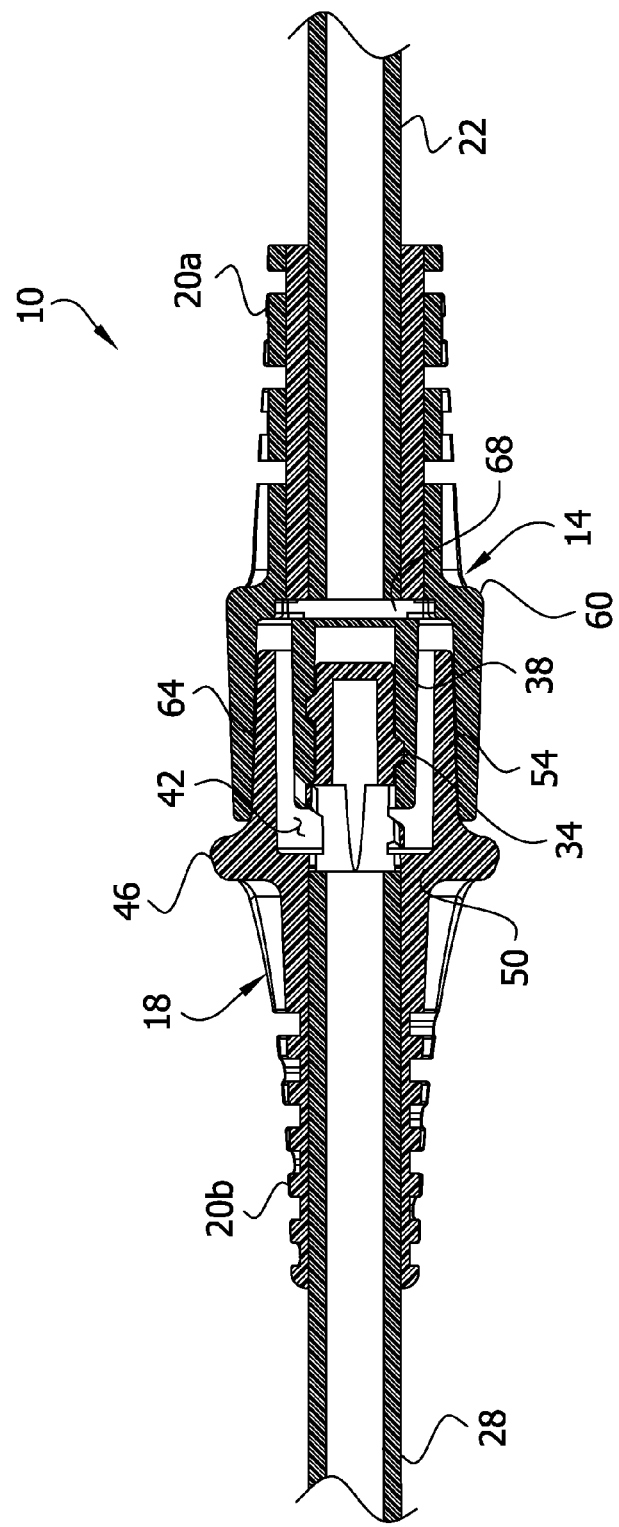
FIG. 3 is a longitudinal section of the connection system of FIG. 2.

Referring to FIGS. 1-3, a discriminating connection system according to this invention is designated generally by the reference 10. In general, system 10 comprises a male threaded locking connector 18 coupled to a first conduit 28, and a female threaded locking connector 14 coupled to a second conduit 22. More specifically, and as best illustrated in FIG. 3, a standoff 34 of the connector 18 includes external threads that thread into a threaded receptacle 38 of the female connector 14 to form a sealed, fluid connection. The standoff 34 and the receptacle 38 may be broadly considered to be a 'discriminating structure'. As will be discussed later, the construction of the male connector 18 prevents connection to other non-conforming connectors or syringes commonly found in medical environments, such as male and female luer-lock connectors and syringes. Similarly, female connector 14 cannot be connected to a wide range of common, non-conforming connectors and syringes. System 10 is configured, when the male connector 18 and the female connector 14 are connected, to permit fluid communication between conduits 22 and 28 in an interior space 42 surrounding the locking mechanism formed by the standoff 34 and the receptacle 38.

Figure 4A:
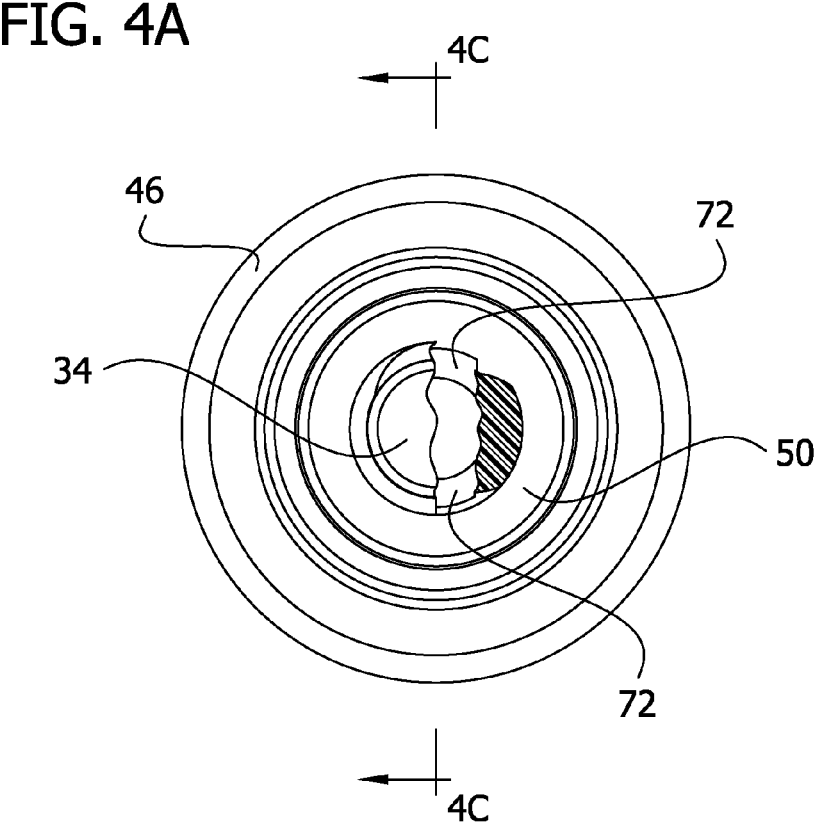
FIG. 4A is a front view of a male connector of the connection system of FIG. 2 with portions of the standoff broken away to show details.
Figure 4B:
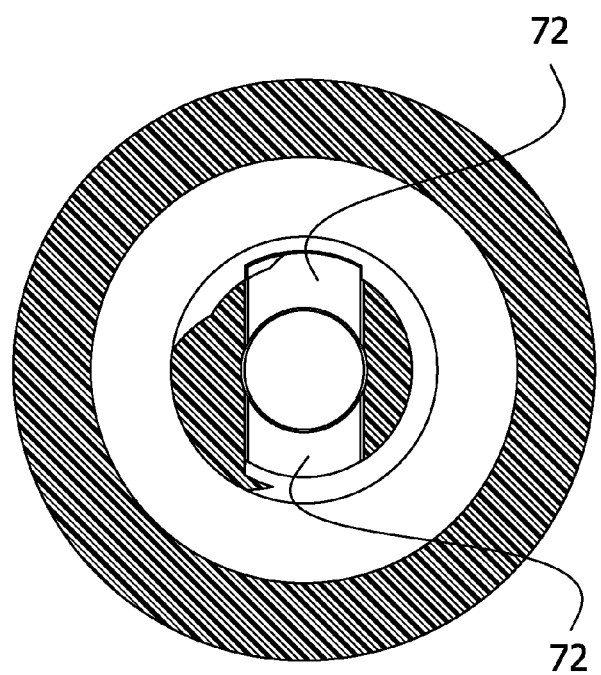
FIG. 4B is a section of the male connector taken in the plane including line 4B-4B of FIG. 4C.
Figure 4C:
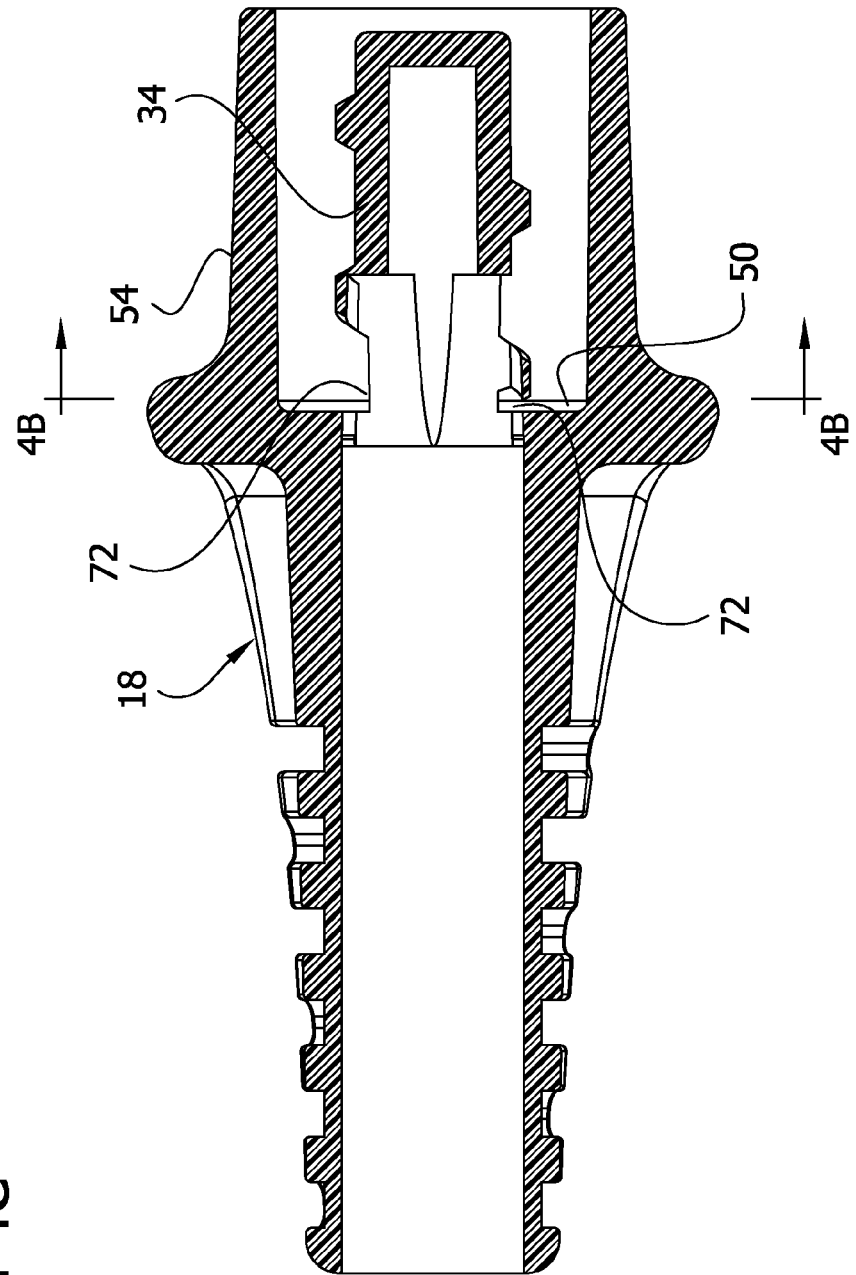
FIG. 4C is a section of the male connector taken in the plane including line 4C-4C of FIG. 4A.

As illustrated in FIGS. 3-4, the male connector 18 includes a generally frustoconical outer annular wall 46, preferably formed with a tapered exterior surface 54 for purposes of custom fit with the female connector 14. Other forms of the annular wall 46, as well as variations in the extent of taper of the surface 54, are within the scope of the invention. The threaded, concentric standoff 34 enclosed within the outer annular wall 46 extends from a floor 50 of the outer member. Though preferably of circular cross section, any suitable thread configuration (form, handedness, thread angle, pitch, etc.) or other type of connection such as a bayonet style connection may be chosen. Moreover, there may be no locking connection between the standoff 34 and the receptacle 38. The floor 50 provides fluid communication between the interior space 42 and the conduit 28 via an arrangement of two openings 72 formed on the floor, as best seen in FIG. 4. Openings 72 are disposed radially outward from the standoff 34. Variations in numbers, design and layout of openings 72 are within the scope of the invention.

Figure 5A:
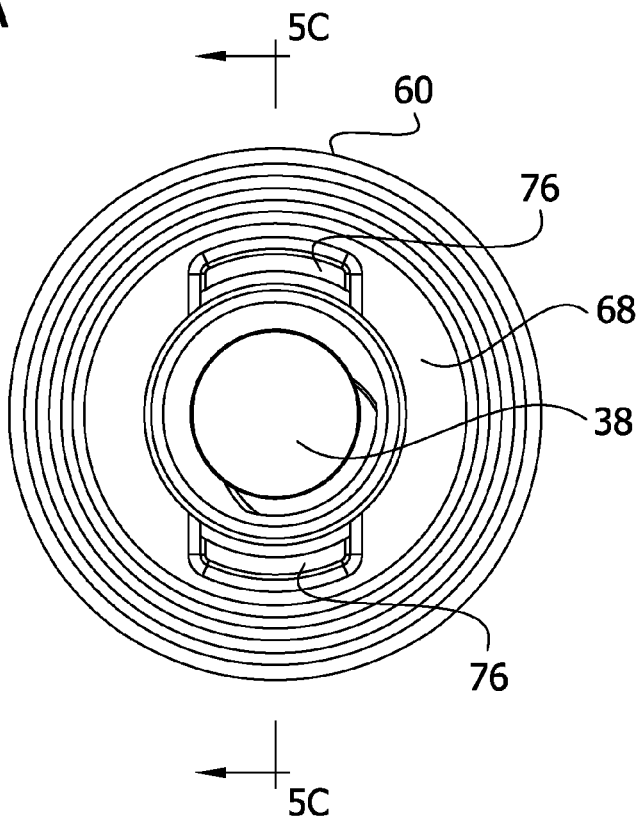
FIG. 5A is a front view of a female connector of the connection system of FIG. 2.
Figure 5B:
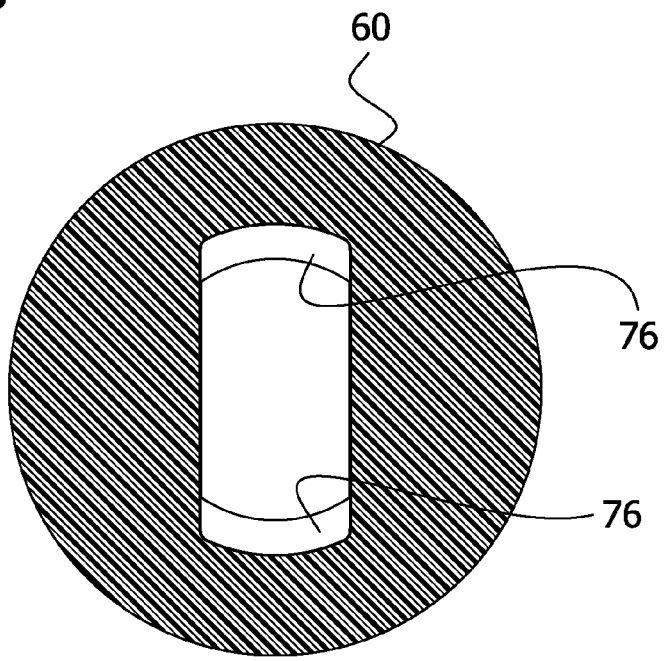
FIG. 5B is a section of the female connector taken in the plane including line 5B-5B of FIG. 5C.
Figure 5C:
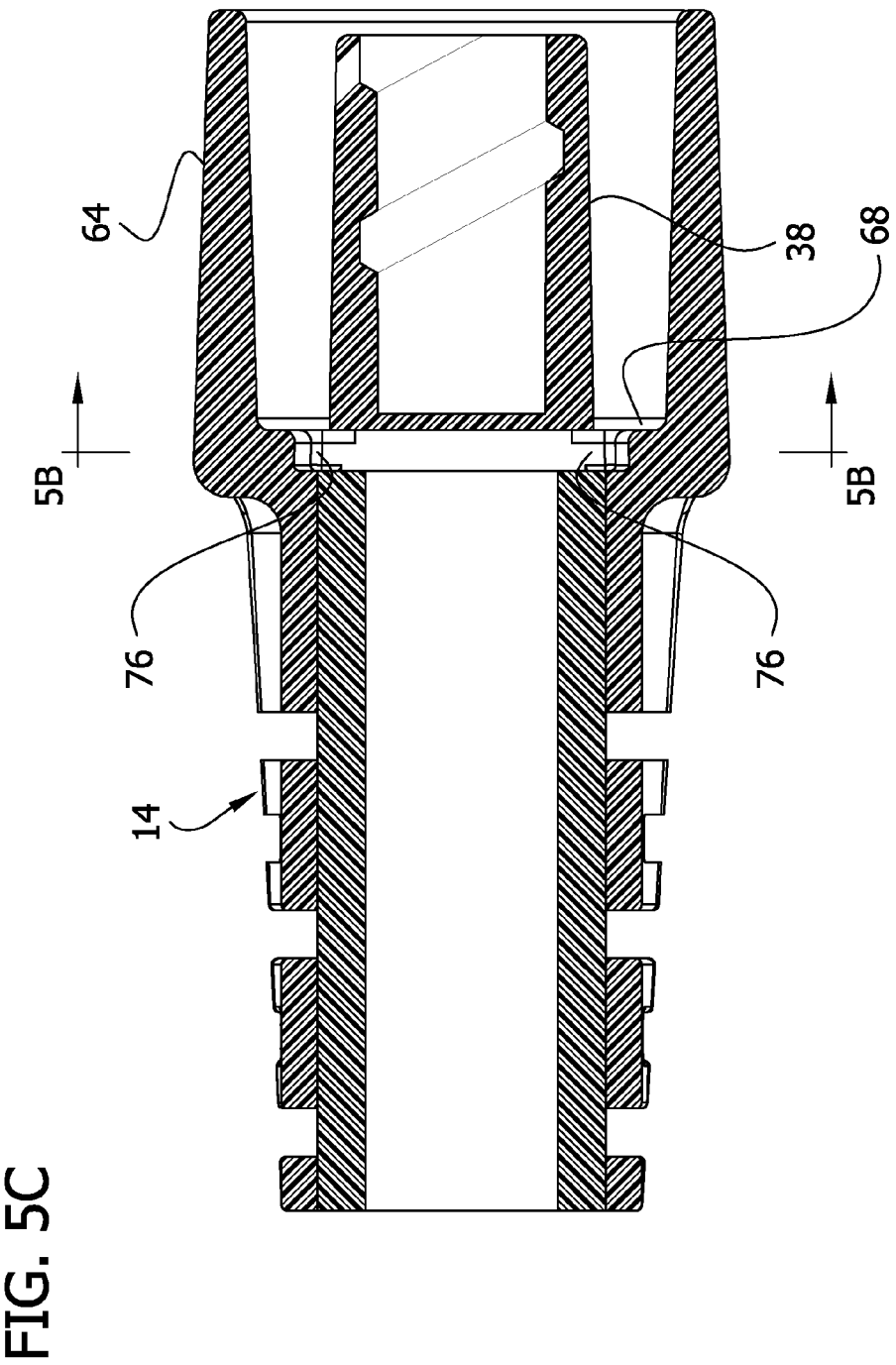
FIG. 5C is a section of the female connector taken in the plane including line 5C-5C of FIG. 5A.

As illustrated in FIGS. 3 and 5, the female connector 14 includes a generally cylindrical outer annular wall 60. The annular wall 60 is preferably formed with a tapering interior surface 64 that receives the tapered outer surface 54 of the frustoconical annular wall 46 of the male connector 18 to form a sealed connection and define an interior space 42. The receptacle 38 extends from a base 68 of the female connector 14. In a preferred embodiment, an inner surface of the receptacle 38 is threaded and sized, complementary to the threading on standoff 34, to thread onto the standoff 34 of the connector 18. As illustrated in FIG. 5, two openings 76 formed on the base 68 of the female connector 14 provide fluid communication between the interior space 42 and the conduit 22. Openings 76 are formed radially outward of the receptacle 38. Variations in numbers, design and layout of openings 76 are within the scope of the invention. In this embodiment, connector system 10 provides separate sealing (tapering surfaces 54, 64) and locking mechanisms (standoff 34, projection 38).

Conduits 22, 28 may be of any suitable form, preferably for medical use. By way of example and not limitation, conduits 22, 28 are associated with enteral feeding sets and/or devices, and the system 10 is used for enteral delivery of medication or nutritional fluids while preventing connectivity with common connectors used for other delivery routes, such as luer lock/slip syringes for intravenous delivery.

Conduits 22, 28 are connected to the female 14 and male connector 18 respectively by any suitable sealing means. Preferably, connectors 14, 18 have strain reliefs 20a, 20b respectively formed thereon for connecting and sealing the respective conduits (see FIGS. 1-3). Advantageously, strain reliefs 20a, 20b allow conduits 22, 28 respectively to flex without breaking away or detaching from the respective connectors 14, 18. In the illustrated embodiment, strain reliefs 20a, 20b are a series of interconnected ridges formed where each conduit meets its respective connector. Other designs of strain relief 20a, 20b are within the scope of the invention. In an embodiment, a tethered cap (not shown) may be formed on each strain relief 20a, 20b for closing off the respective connector during non-use. Each tethered cap may be integrally formed or molded with its respective strain relief. Alternatively, the tethered cap may be formed on the connector itself.

Strain reliefs 20a, 20b are formed of any suitable flexible material. In contrast, connectors 14, 18 are preferably rigid and not flexible or conformable, thereby preventing forced accommodation of non-conforming connectors. This permits the connectors to form a tapering, interference fit of a sealing nature as described below.

Figure 6:
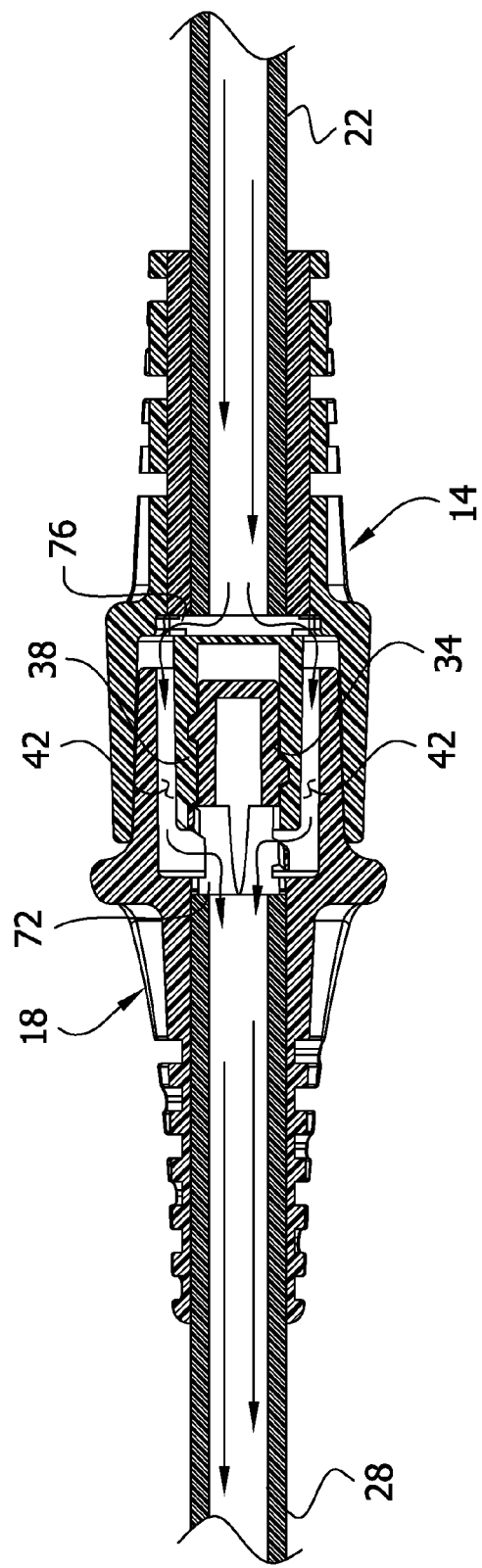
FIG. 6 is a longitudinal section illustrating fluid flow through the connection system of FIG. 3.
Figure 7A:
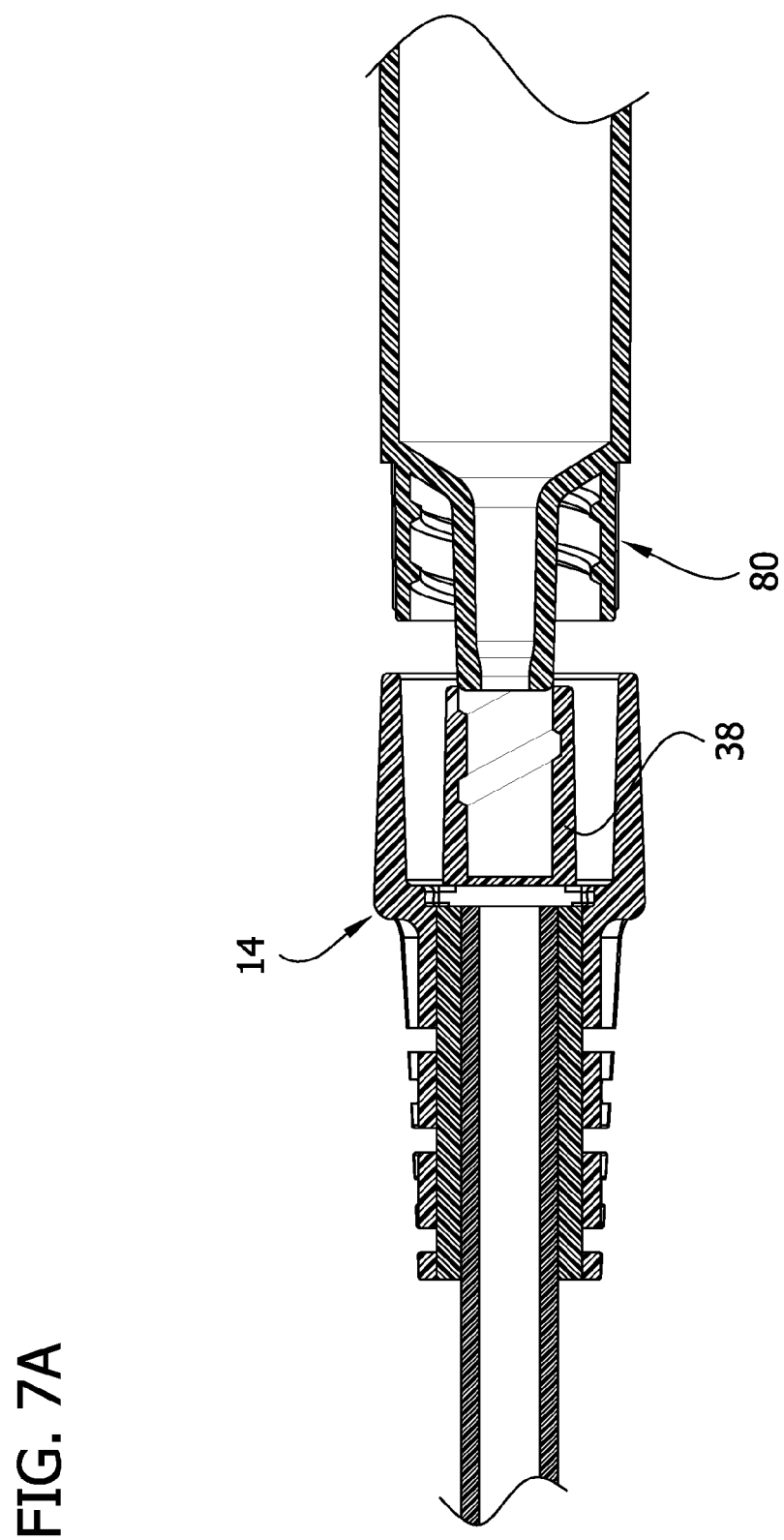
FIG. 7A is a sectional view of a failed connection between the female connector and a male luer-lock type syringe.
Figure 7B:
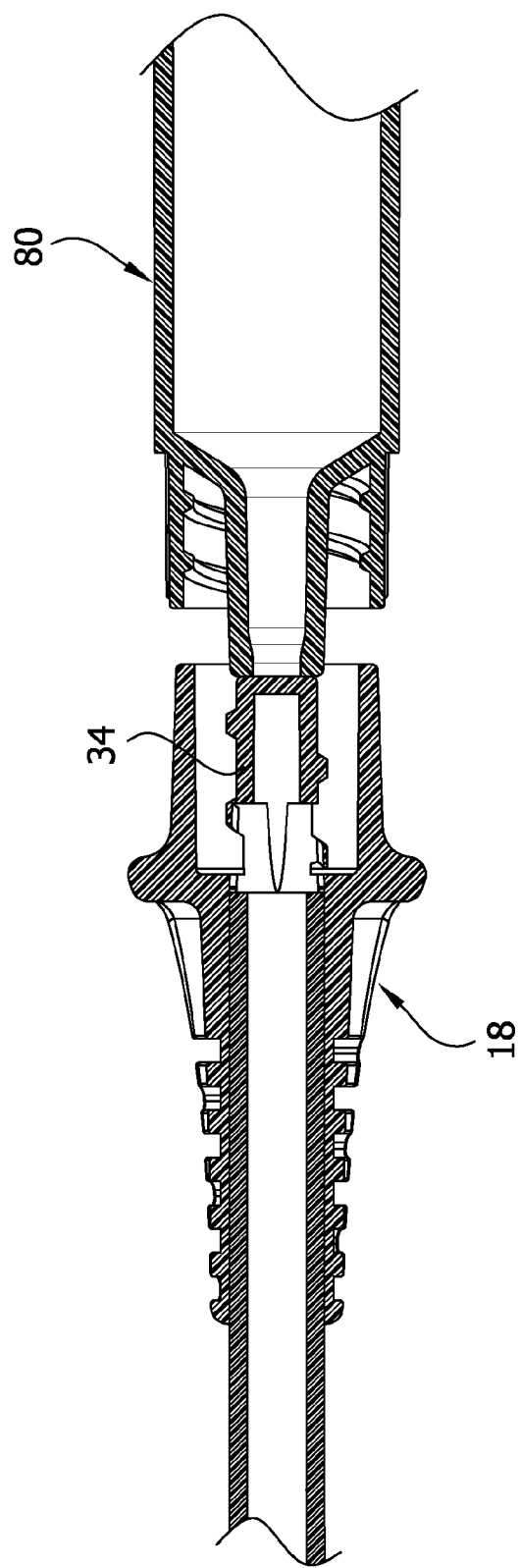
FIG. 7B is a sectional view of a failed connection between the male connector and a male luer-lock type syringe.
Figure 7C:
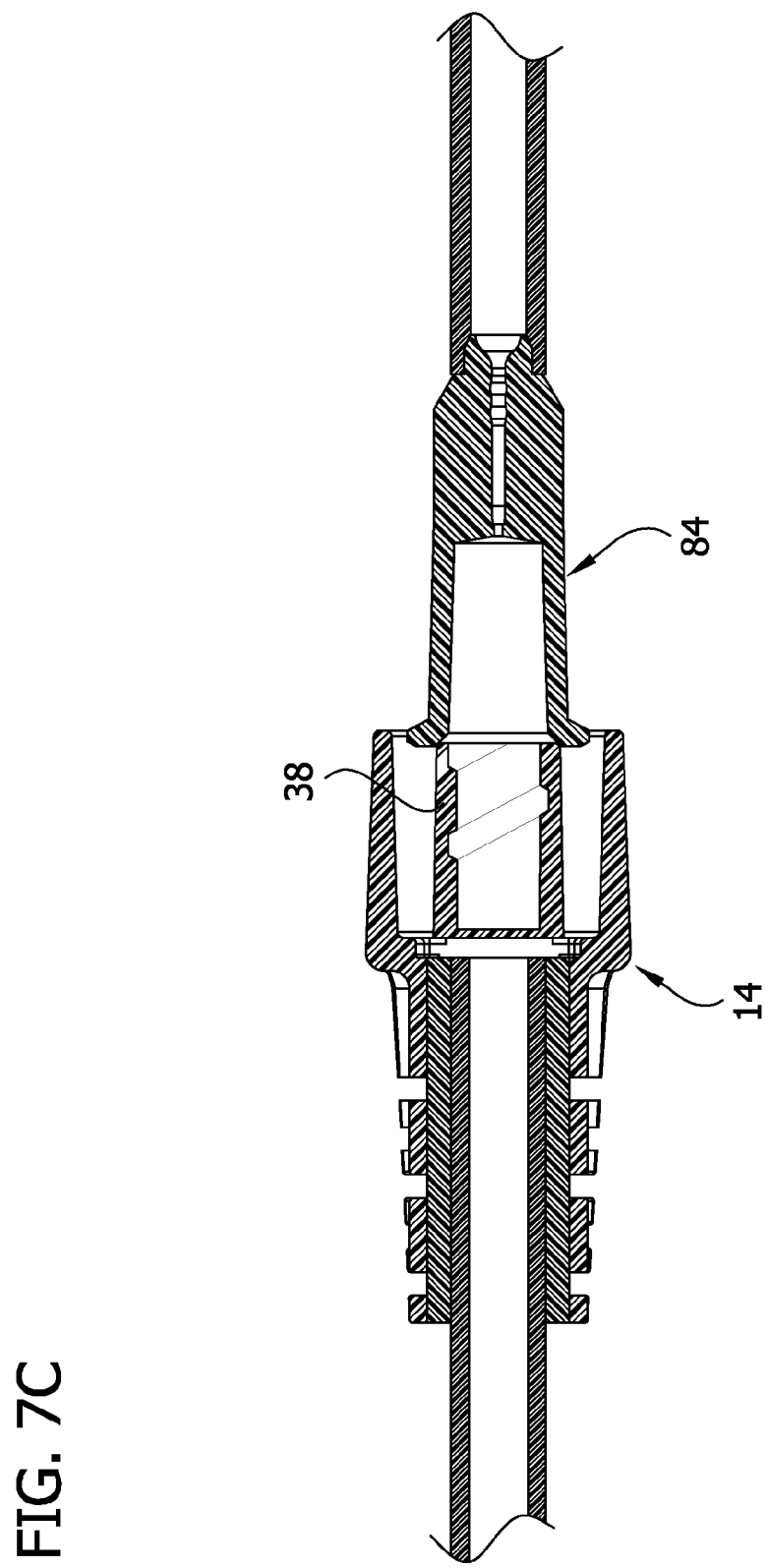
FIG. 7C is a sectional view of a failed connection between the female connector and a female luer-lock type syringe.
Figure 7D:
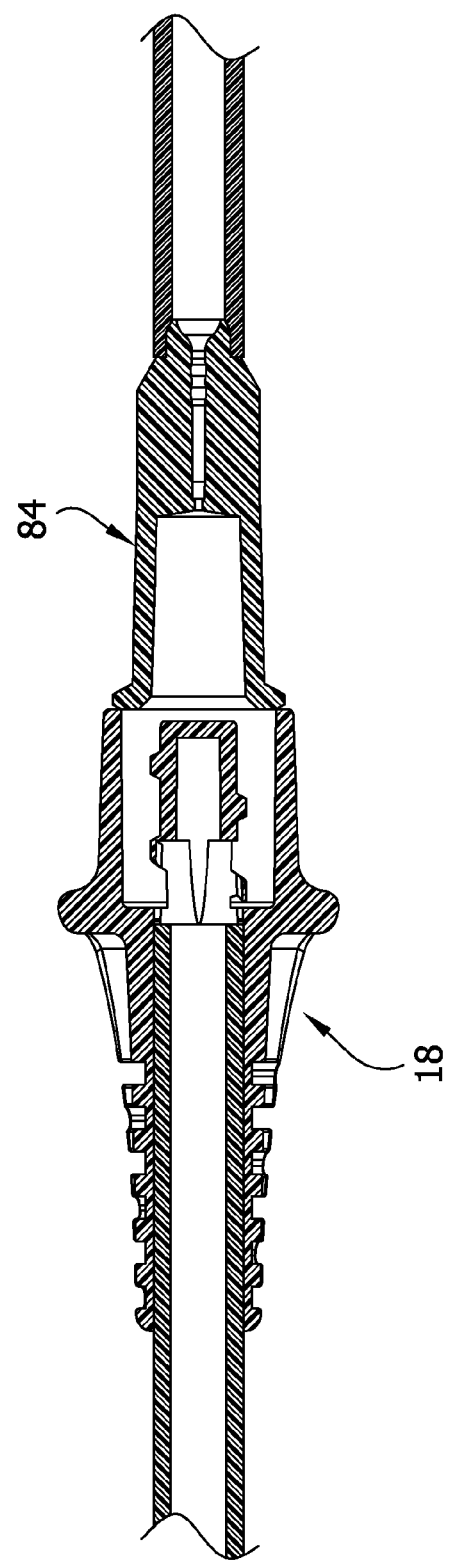
FIG. 7D is a sectional view of a failed connection between the male connector and a male luer-lock type syringe.
Figure 7E:
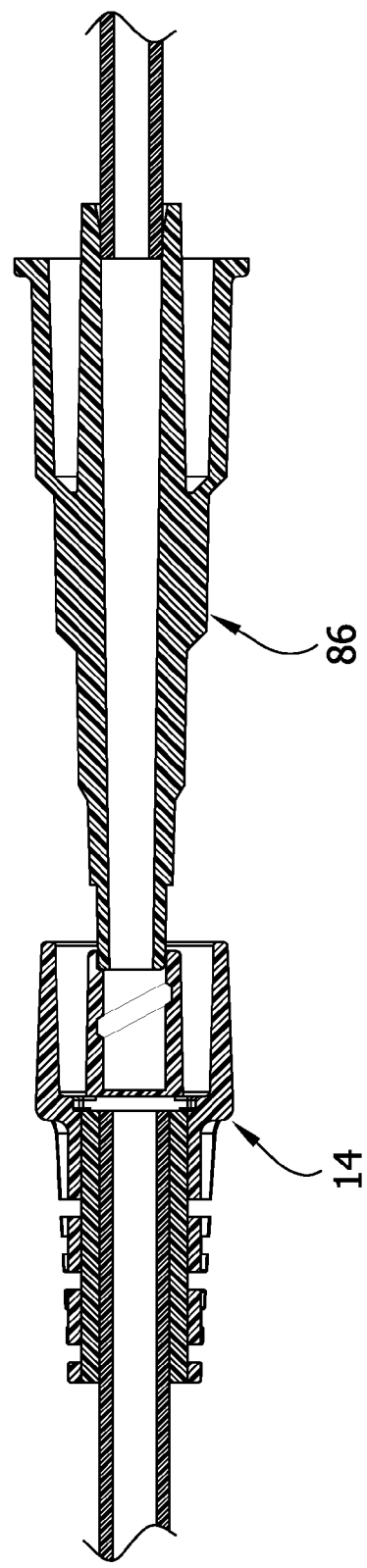
FIG. 7E is a sectional view of a failed connection between the female connector and a stepped connector having a luer tip.
Figure 7F:
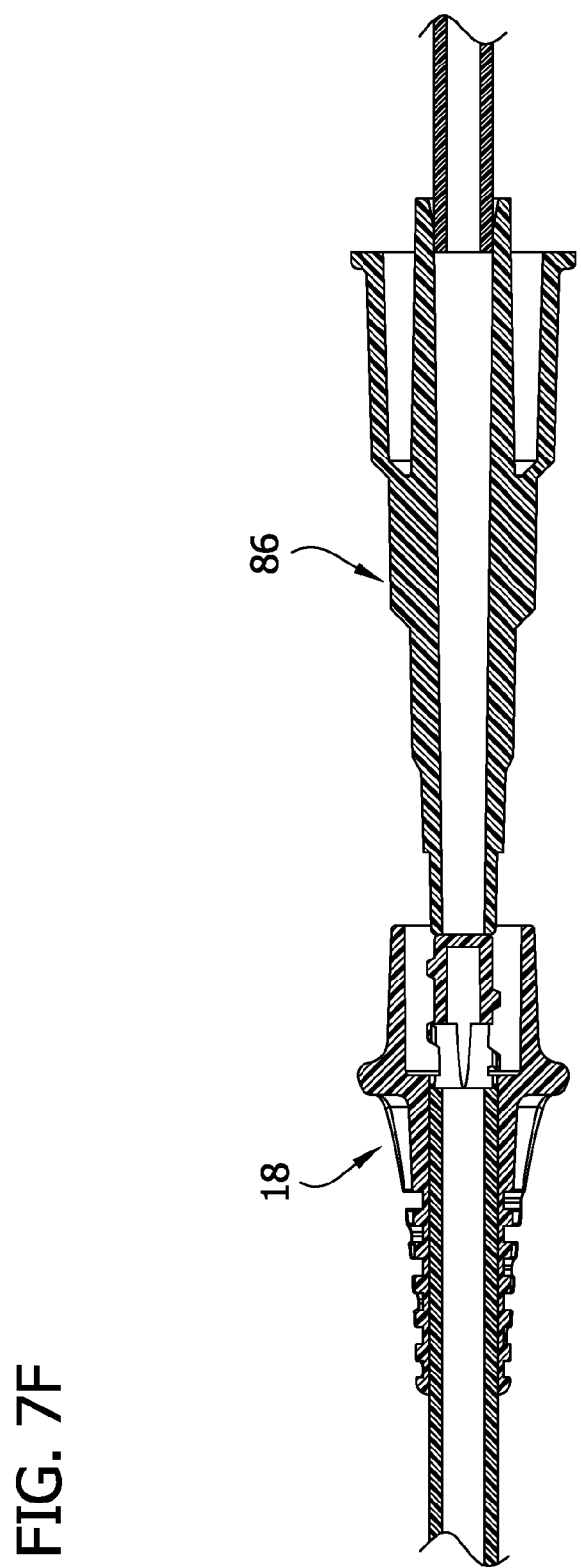
FIG. 7F is a sectional view of a failed connection between the male connector and a stepped connector having a luer tip.

FIG. 6 illustrates fluid flow through the mated female and male connectors 14, 18. To mate the connectors, they are pushed together to bring standoff 34 into the receptacle 38. One or both of the connectors 14, 18 are rotated to engage the threads of the standoff 34 and receptacle 38 and to draw the annular walls 60, 46 into sealing engagement. In a typical medical application, fluid flows from the feeding set via a source line 22, through openings 76 of the female connector 14 and into the interior space 42. Flow continues through openings 72 of the connector 18 and into a delivery line 28 for delivery to the patient. By virtue of positioning of openings 72 and 76, the fluid flows around the centrally located standoff 34 and receptacle 38.

FIG. 7 illustrates how connections of either the male connector 18 or the female connector 14 discriminate non-conforming connectors and in particular luer-type connectors. FIG. 7A shows a failed connection between the female connector 14 and a male luer-lock syringe 80. The luer tip engages but cannot enter the receptacle 38, so that connection is not achieved. FIG. 7B shows a failed connection between the male connector 18 and the male luer-lock syringe 80. This time, the standoff 34 engages the luer tip of the syringe 80, preventing mating. FIGS. 7C and 7D show how a female luer connector 84 abuts the receptacle 38 and the annular wall 46, and is unable to connect to the female connector 14 or the male connector 18, respectively. FIGS. 7E and 7F illustrate a mismatch between the female connector 14 and a stepped connector 86 having a luer tip and between the male connector 18 and the stepped connector, respectively.

Figure 8A:
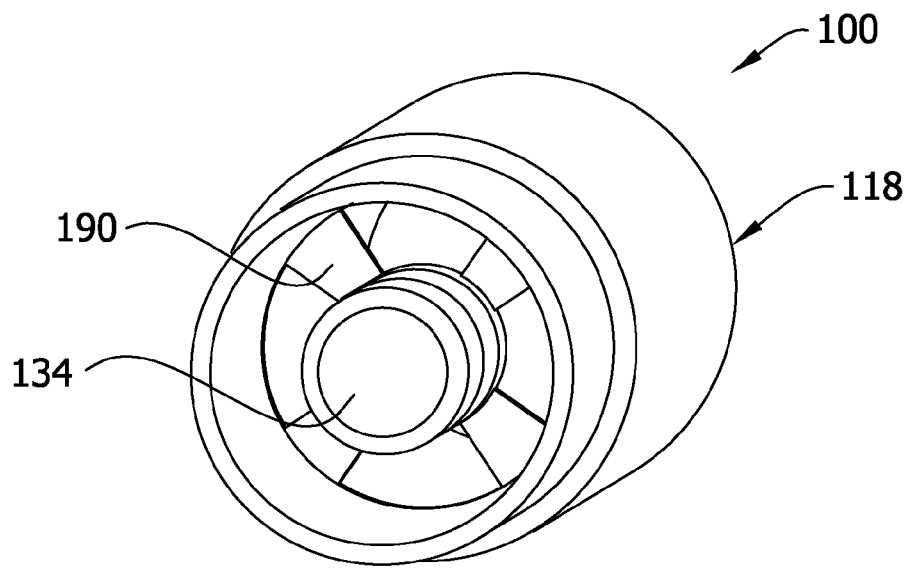
FIG. 8A is a front perspective of a male connector having a web-like structure according to another embodiment of the invention.
Figure 8B:
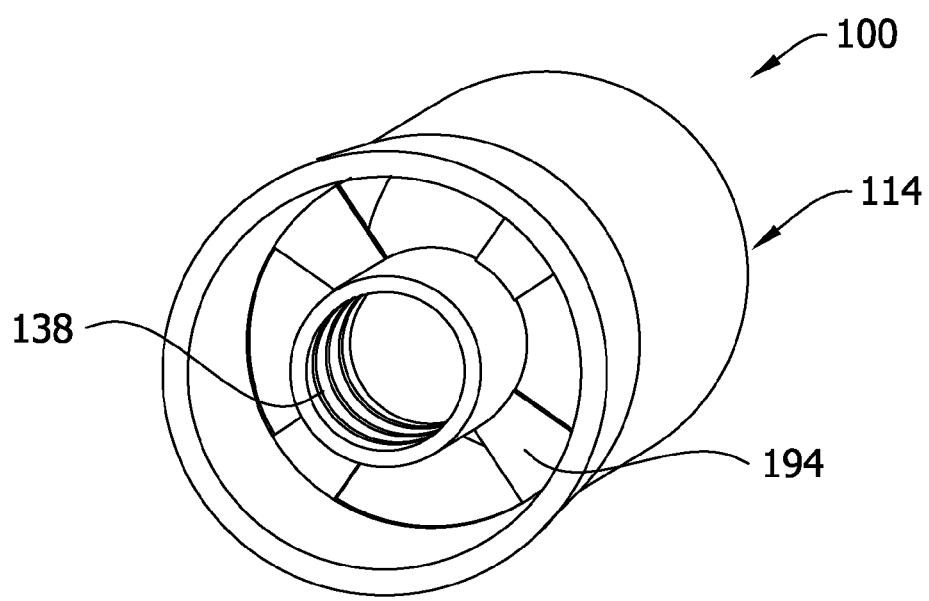
FIG. 8B is a front perspective of a female connector having a web-like structure and corresponding to the male connector of FIG. 8A.

In another embodiment of a connection system 100 shown (as separate components) in FIG. 8, the floor of the connector 118 is modified to provide a web-like structure 190 for holding the threaded standoff 134 in place. The base of the female connector 114 is similarly modified with a web-like structure 194 to hold threaded receptacle 138 in place. A fluid path 198 is then formed upon sealed connection between connectors 114 and 118.

Figure 9A:
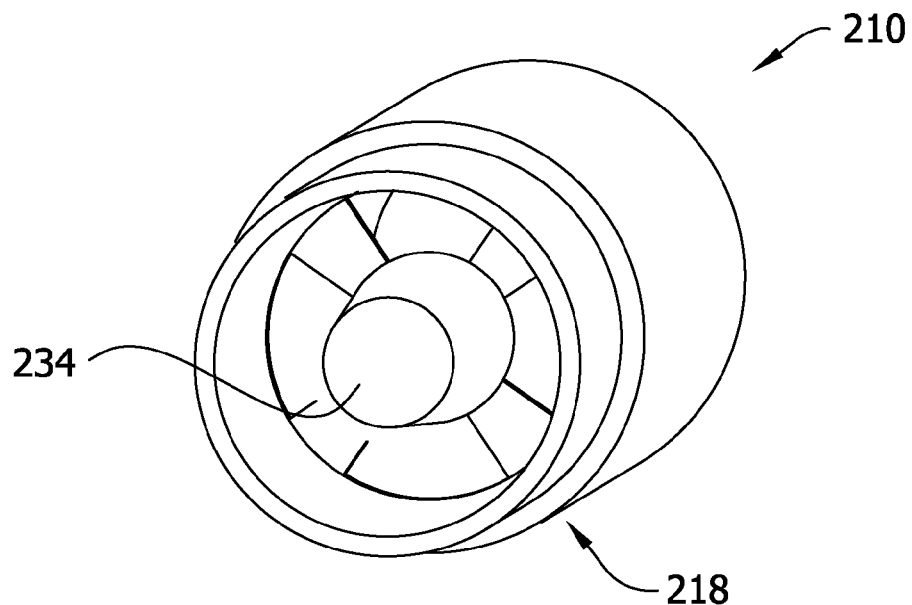
FIG. 9A is a front perspective of a male connector having a tapered standoff according to another embodiment of the invention.
Figure 9B:
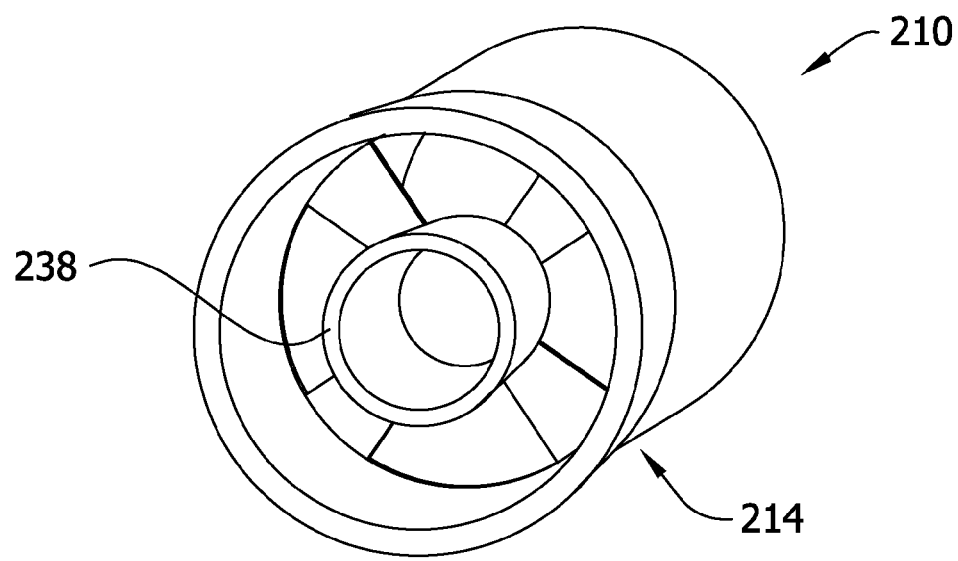
FIG. 9B is a front perspective of a female connector having a tapered receptacle and corresponding to the male connector of FIG. 9B.

In yet another embodiment (see FIG. 9), the locking mechanism of the connection system 210 is a tapered-locking mechanism. Male connector 218 has an unthreaded tapered standoff 234, generally conical, that forms a sliding interference fit with an unthreaded and tapered receptacle 238 of the female connector 214. The other components of the tapered-locking connection system may or may not be similar to that of the threaded-locking connection system.

Figure 10:
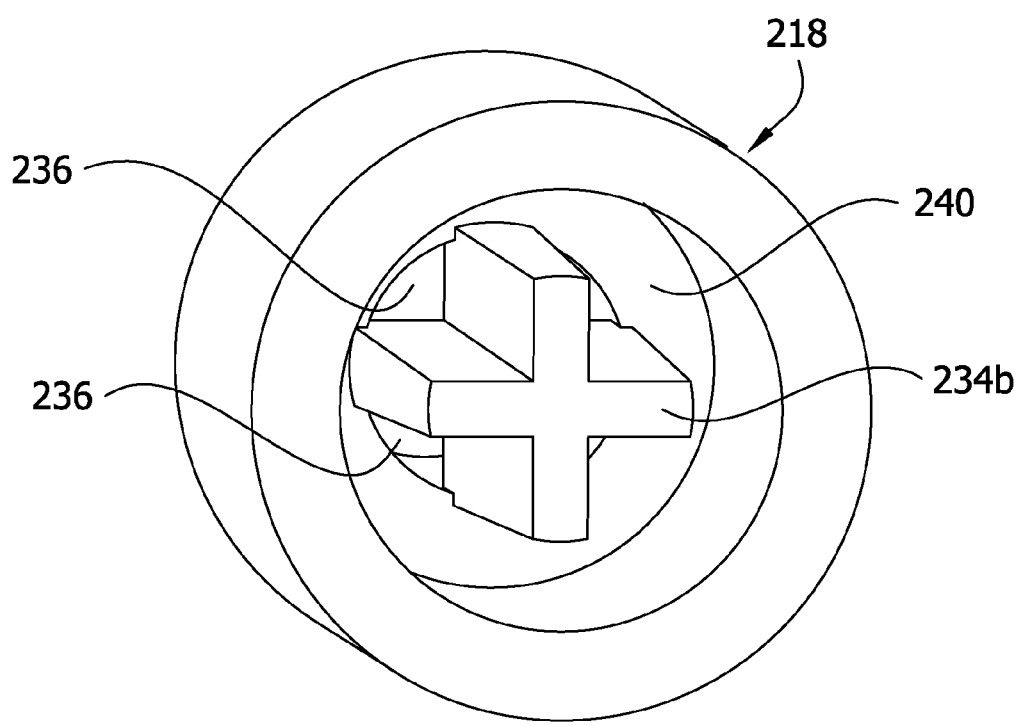
FIG. 10 is a front perspective of an alternate design of the tapered standoff of FIG. 9A.

In yet another embodiment conceptually illustrated in FIG. 10, male connector 218 has a tapered, cross-shaped standoff 234b, instead of the solid standoff 234. Openings 236 are formed on the floor 240 within the footprint of the cross-shaped standoff 234b. Standoff 234b is sized to provide a sliding interference fit with receptacle 238 (FIG. 9B) without the receptacle touching the floor 240, thereby preventing blockage of openings 236. Other variations of the shape of standoff 234b that permit access to openings 236 when in a sealed configuration are within the scope of the invention.

The conduits 22 and 28, male connector 18 and female connector 14 are formed of generally biocompatible and non-reactive materials. The conduits 22, 28 are preferably flexible medical tubing, while male connector 18 and female connector 14 are preferably semi-rigid and formed of suitable materials. Different materials may be used to form the locking mechanism and the sealing mechanism, providing some freedom of selecting design, rigidity, etc.

Figure 11:
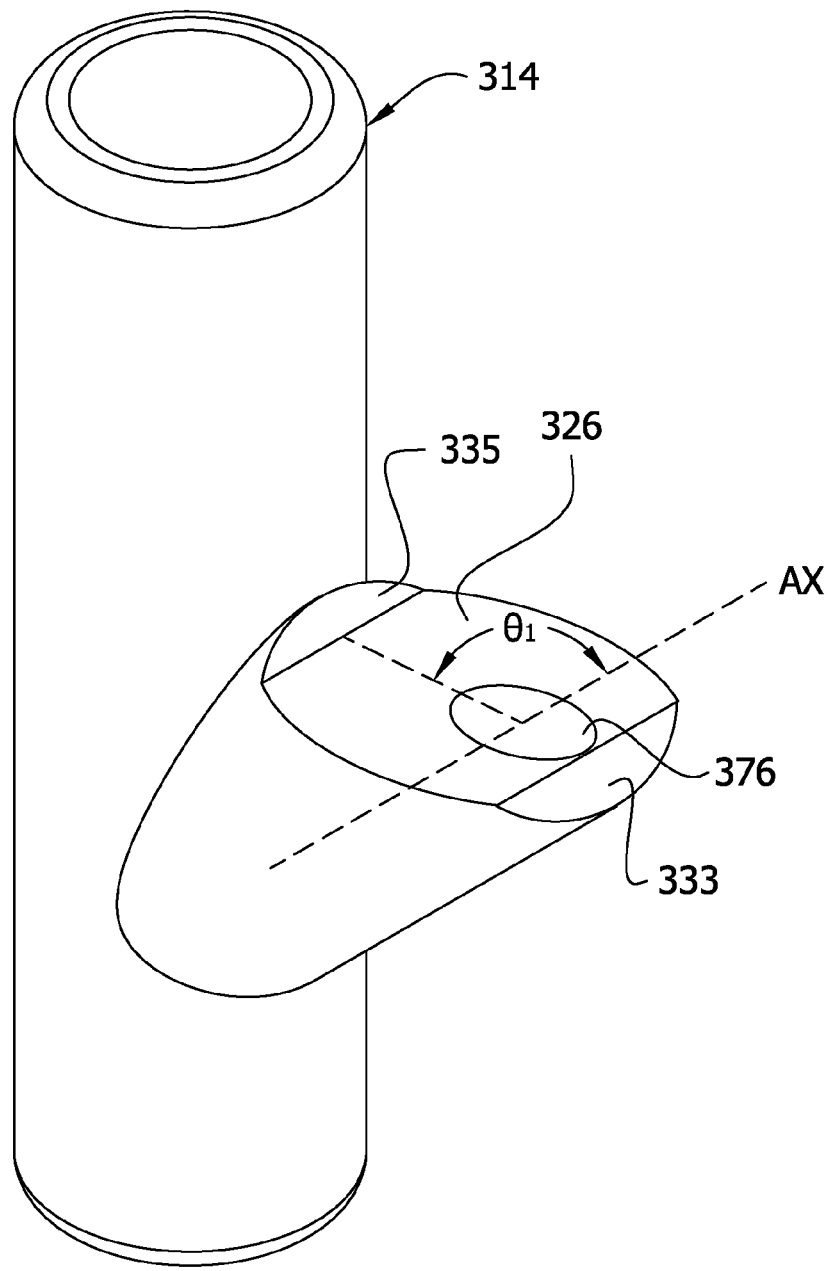
FIG. 11 is a fragmentary perspective of a female connector according to another embodiment of the invention.
Figure 12A:
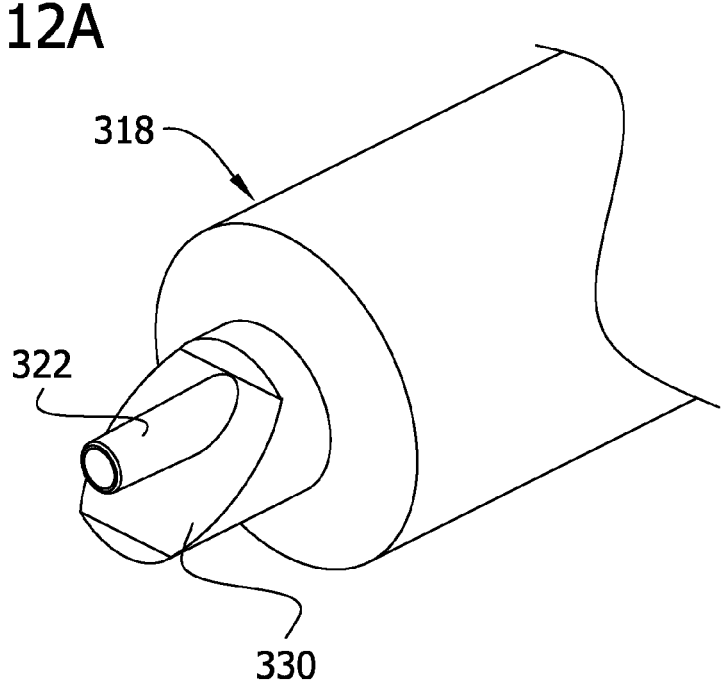
FIG. 12A is a fragmentary perspective of a male connector for use with the female connector of FIG. 11.
Figure 12B:
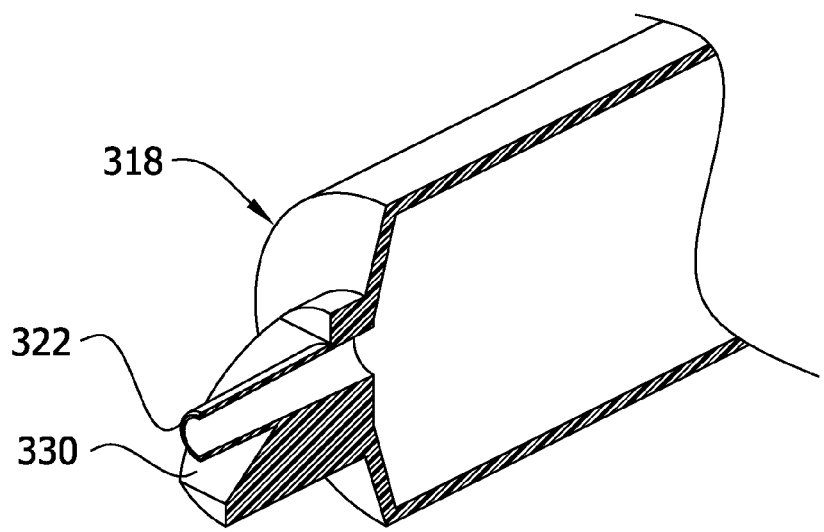
FIG. 12B is the male connector of FIG. 12A in section.
Figure 13A:
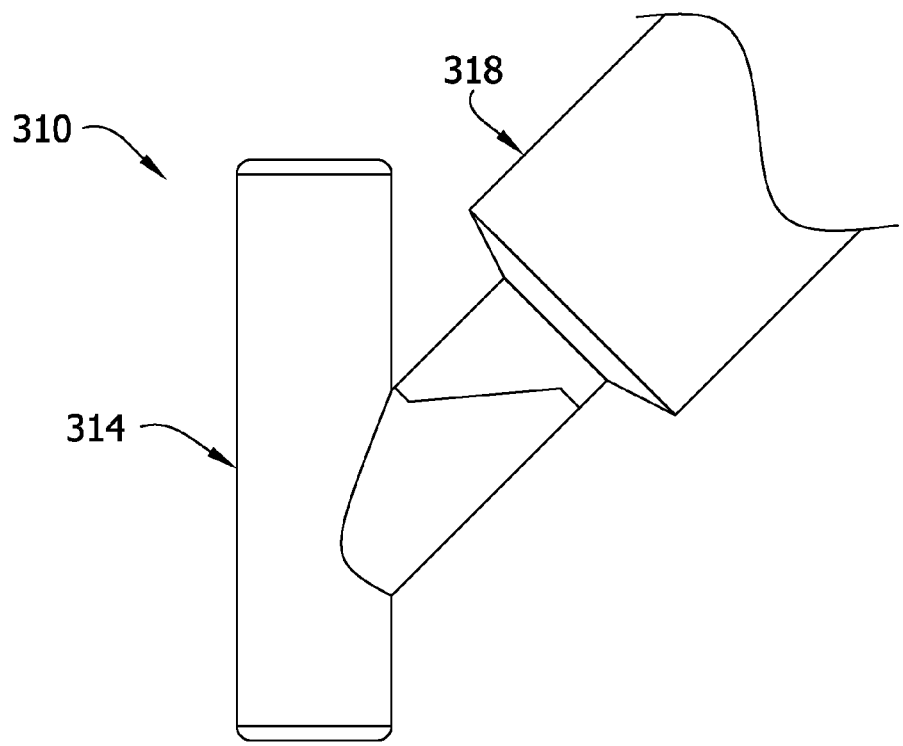
FIG. 13A is an elevation of a connection system comprising the female, male connectors of FIGS. 11, 12A respectively.
Figure 13B:
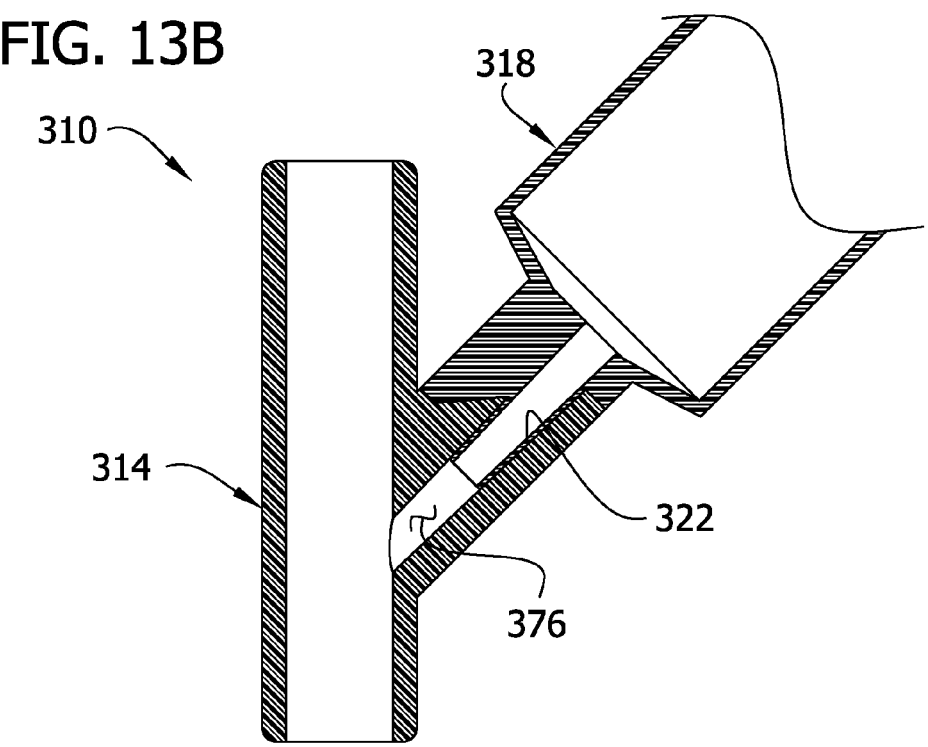
FIG. 13B is a section of the connection system of FIG. 13A.

FIGS. 11-13 illustrate still another embodiment of a connector system 310 for enteral delivery that incorporates anti-luer, discriminating connector concepts of the invention. A female connector 314 has a passage 376 that mates with a tip 322 of a syringe 318. The female connector 314 also has a sculpted mating surface 326 that mates with a complementary sculpted surface 330 surrounding the tip 322. Desirably, and as illustrated, the plane of the surface 326 is angled with respect to an axis AX of passage 376. Angle $\theta_1$ is generally obtuse, and desirably selected to provide non-conformance with luer-lock and luer-slip syringes. Surface 326 may include variations in plane, such as subsurfaces 333 and 335, to require custom connectors for proper fit. Accordingly, surface 330 is shaped to complement surface 326 for proper fit as best illustrated in FIGS. 12A and 12B. The sculpted shapes warn the user that standard syringes and connectors should not be used.

Figure 14A:
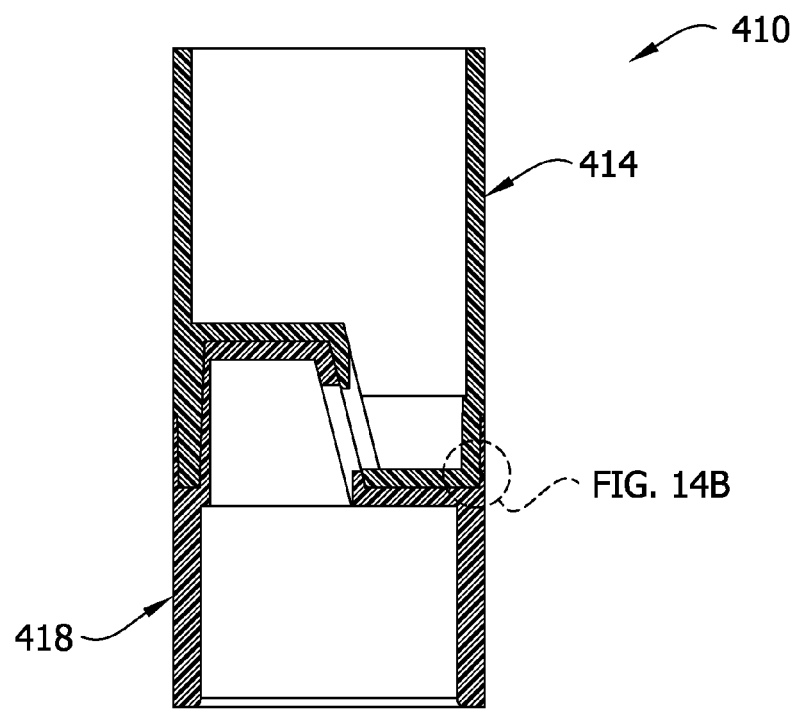
FIG. 14A is a fragmentary vertical section of a connection system according to another embodiment of the invention.
Figure 14B:
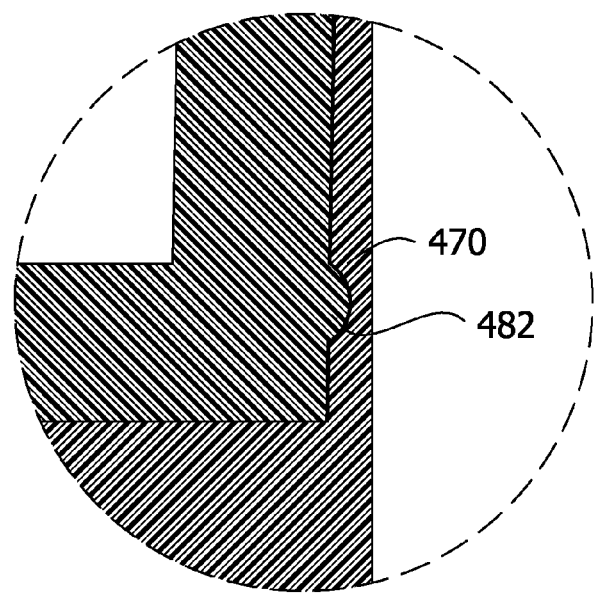
FIG. 14B is an enlargement of a fragment of FIG. 14A.
Figure 15A:
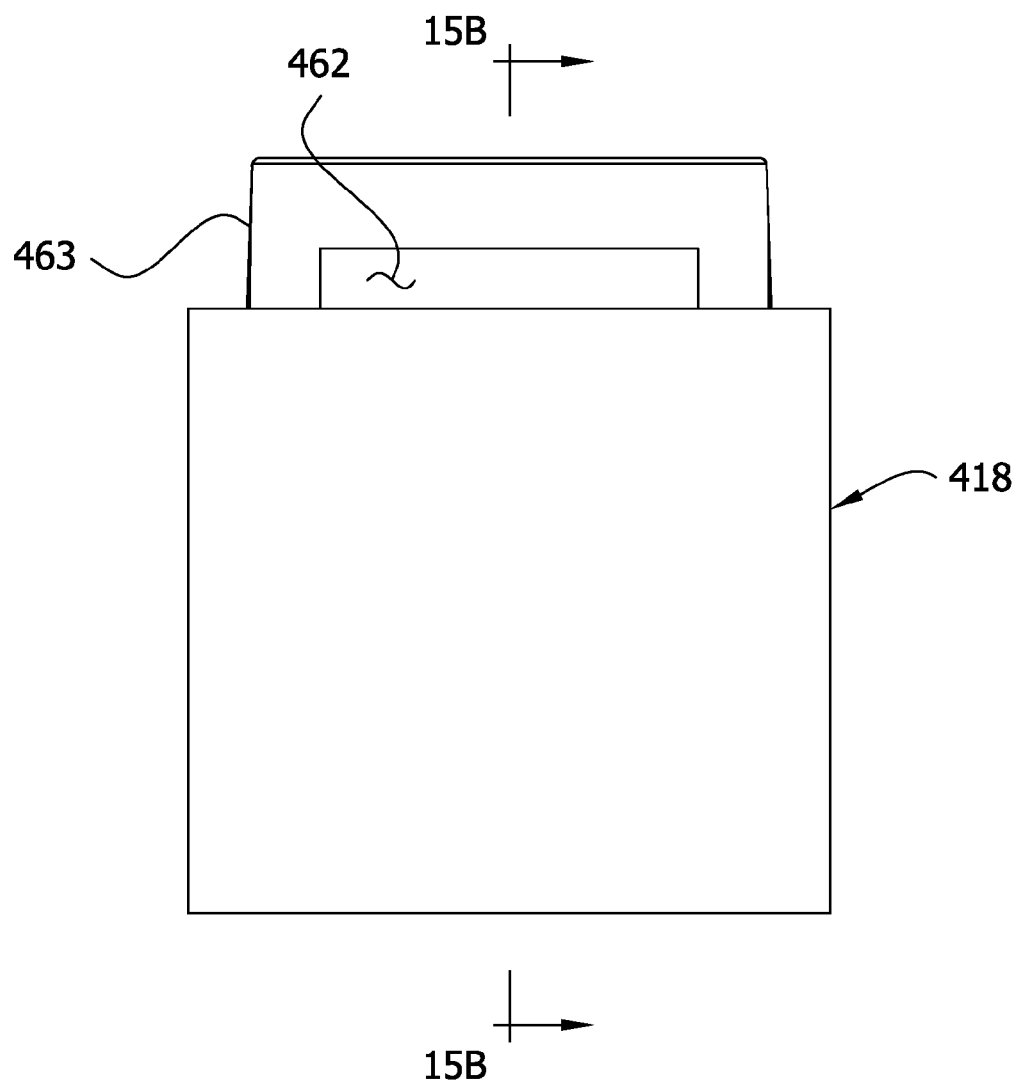
FIG. 15A is a front view of a port of the connection system of FIG. 14A.
Figure 15B:
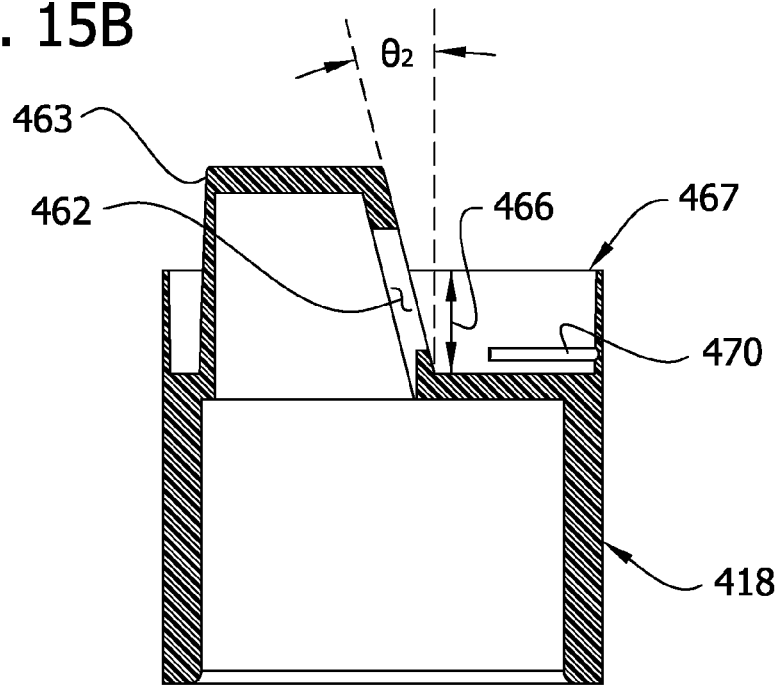
FIG. 15B is a section of the port of FIG. 15A taken in a plane including line 15B-15B of FIG. 15A.
Figure 15C:
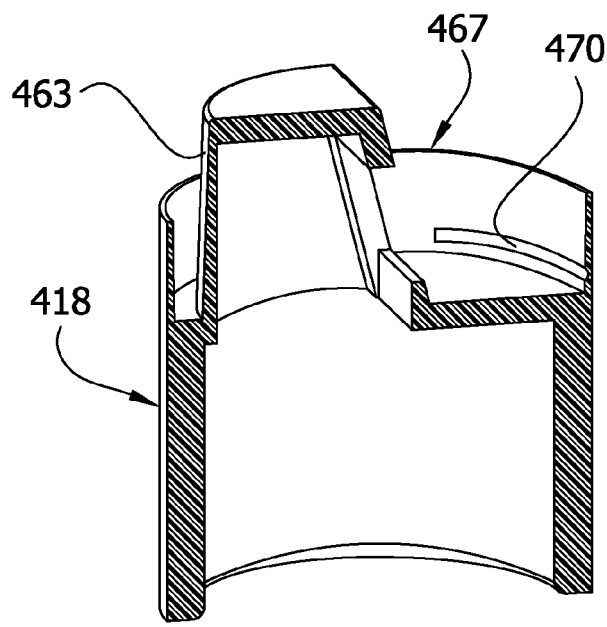
FIG. 15C is an elevation of the port of FIG. 15B.
Figure 16A:
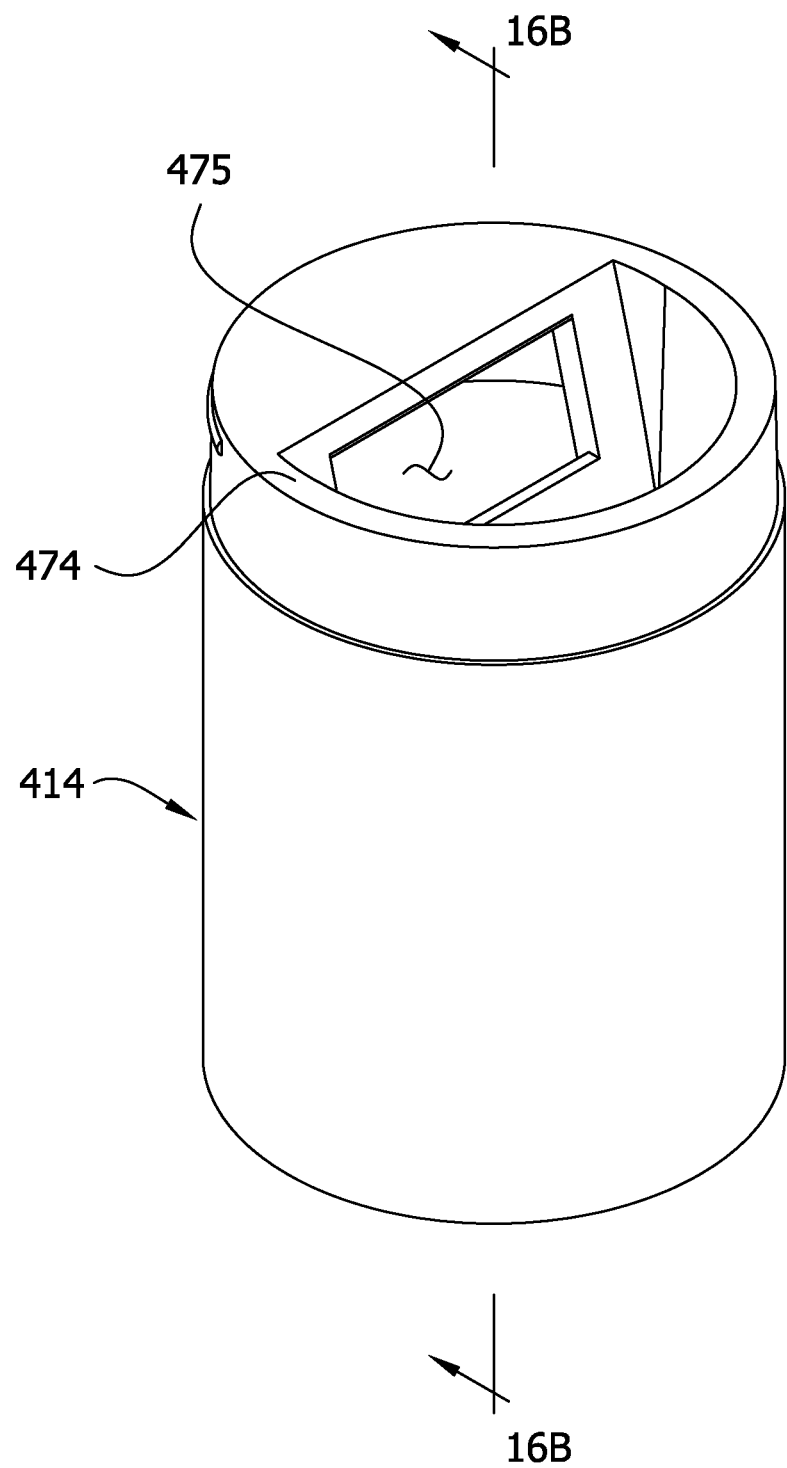
FIG. 16A is a top perspective of a syringe of the connection system of FIG. 15A.
Figure 16B:
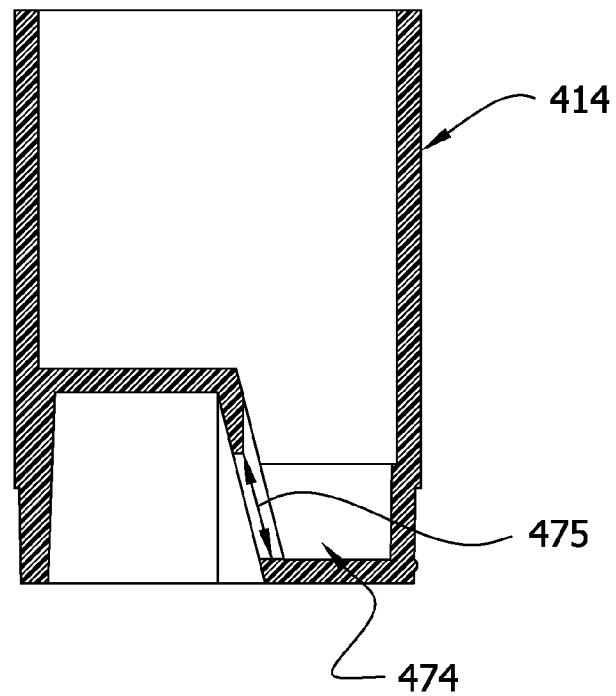
FIG. 16B is a section of the syringe of FIG. 16A taken in the plane including line 16B-16B of FIG. 16A.
Figure 16C:
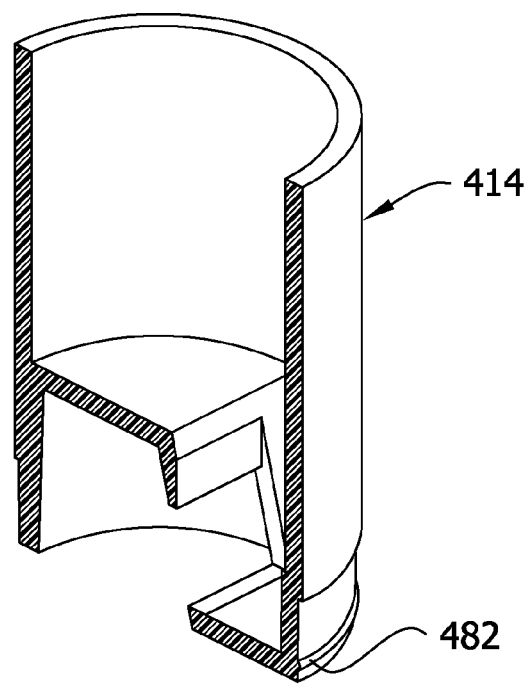
FIG. 16C is an elevation of the syringe of FIG. 16B.

In another embodiment illustrated in FIGS. 14-16, a connector system 410 comprises a port 418 and a syringe 414. Port 418 has a generally rectangular opening 462 in a projecting part 463 at the end of the port. The opening 462 allows for passage of fluid into or out of the port 418. Shapes of the port opening 462 other than rectangular are within the scope of the invention. Projecting part 463 has a surface that is preferably angled away from the axis of the port 418. This angle $\theta_2$ may be selected such that a standard luer-type syringe would need to be presented in an angular fashion to access the opening 462, although the opening is not sized or shaped to receive a luer tip. Port 418 further comprises an annular port wall 466 defining a receptacle 467 for receiving and sealing with the syringe 414. Port wall 466 also restricts access to the opening 462 in a manner that prevents angular insertion of luer-type syringes as described above. Port wall 466 tapers towards its free edge. A recess 470 is cut into the port wall 466, the use of which is described hereinafter.

The syringe 414 has an end that is shaped in a manner complementary to that of the port 418. The syringe 414 is broadly 'a connector'. The end of the syringe 414 is radially inset for being received in the receptacle 467 of the port 418. The end has a semicircular recess 474 sized and shaped to receive the projecting part 463 of the port 414. An opening 475 in an angled wall in the recess 474 is aligned with the opening 462 in the projecting part 463 when the port 418 and syringe 414 are connected for fluid communication. A bump 482 on the end of the syringe 414 snaps into the recess 470 on the port 418 for secure, temporary connection and sealing (see FIG. 14B).

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained. The invention significantly reduces the risk of using erroneous (especially intravenous) routes of administration, as none of the components of the connector systems of the invention are compatible with luer-lock or luer-slip syringes.

As various changes could be made in the above constructions without departing from the scope of the invention, it is intended that all matter contained in the above description and shown in the accompanying drawing shall be interpreted as illustrative and not in a limiting sense.

What is claimed is:

1. An enteral feeding connection system for forming a sealed fluid connection for use in delivering nutritional fluids to a patient, said system comprising:
a first enteral feeding connector configured for attachment to a first enteral feeding tube for receiving nutritional fluids to be delivered to the patient, the first enteral feeding connector comprising a floor, an annular wall extending from the floor, a standoff projecting from the floor within the annular wall and disposed for blocking nonconforming connectors from entering into fluid connection with the annular wall of the first enteral feeding connector, and an opening in one of the standoff and the floor;
a second enteral feeding connector configured for attachment to a second enteral feeding tube for receiving the nutritional fluids to be delivered to the patient, the second enteral feeding connector comprising a floor, an annular wall adapted to form a sealed fit connection with the annular wall of the first enteral feeding connector to provide a fluid tight passage between the first and second enteral feeding connectors, a receptacle projecting from the floor of the second enteral feeding connector to receive the standoff of the first enteral feeding connector and permit the annular wall of the first enteral feeding connector to come into sealing engagement with the annular wall of the second enteral feeding connector to form said fluid tight passage, and an opening in the floor of the second enteral feeding connector disposed radially outward from the receptacle;
wherein connecting the first enteral feeding connector and the second enteral feeding connector provides a fluid-tight connection between said first enteral feeding tube and said second enteral feeding tube when both of the first and second enteral feeding tubes are attached to the respective connectors so that the nutritional fluid may be delivered from the second enteral feeding tube through the enteral feeding connectors and to the first enteral feeding tube for enteral delivery of the nutritional fluid to the patient; and
a locking mechanism for locking the first and second enteral feeding connectors together, wherein the locking mechanism comprises threads on an exterior surface of the standoff and threads on an interior surface of the receptacle.

2. The connector system of claim 1 wherein the first enteral feeding connector standoff is sized to prevent a fluid-tight connection with a male luer connector.

3. The connector system of claim 1 wherein the second enteral feeding connector receptacle is sized to prevent a fluid-tight connection with male and female luer connectors.

4. The connector system of claim 1 wherein the annular wall of the first enteral feeding connector has an axially tapering outer surface and the annular wall of the second enteral feeding connector has an axially tapering inner surface for receiving the tapering outer surface of the first enteral feeding connector.

5. The connector system of claim 1 wherein the first and second enteral feeding connectors are formed of a generally biocompatible and non-reactive material.

6. The connector system of claim 1 in combination with the first and second enteral feeding tubes.

7. The connector system of claim 1 wherein the first enteral feeding connector has a longitudinal axis and the standoff is generally coaxial with the longitudinal axis of the first enteral feeding connector.

8. The connector system of claim 7 wherein the second enteral feeding connector has a longitudinal axis and the receptacle is generally coaxial with the longitudinal axis of the second enteral feeding connector.

9. An enteral feeding connection system for forming a sealed fluid connection for use in delivering nutritional fluids to a patient, said system comprising:
a first enteral feeding connector configured for attachment to a first enteral feeding tube for receiving nutritional fluids to be delivered to the patient, the first enteral feeding connector comprising a floor, an annular wall extending from the floor, a standoff projecting from the floor within the annular wall and disposed for blocking nonconforming connectors from entering into fluid connection with the annular wall of the first enteral feeding connector, and an opening in one of the standoff and the floor; and
a second enteral feeding connector configured for attachment to a second enteral feeding tube for receiving the nutritional fluids to be delivered to the patient, the second enteral feeding connector comprising a floor, an annular wall adapted to form a sealed fit connection with the annular wall of the first enteral feeding connector to provide a fluid tight passage between the first and second enteral feeding connectors, a receptacle projecting from the floor of the second enteral feeding connector to receive the standoff of the first enteral feeding connector and permit the annular wall of the first enteral feeding connector to come into sealing engagement with the annular wall of the second enteral feeding connector to form said fluid tight passage, and an opening in the floor of the second enteral feeding connector disposed radially outward from the receptacle;
wherein connecting the first enteral feeding connector and the second enteral feeding connector provides a fluid-tight connection between said first enteral feeding tube and said second enteral feeding tube when both of the first and second enteral feeding tubes are attached to the respective connectors so that the nutritional fluid may be delivered from the second enteral feeding tube through the enteral feeding connectors and to the first enteral feeding tube for enteral delivery of the nutritional fluid to the patient;
wherein when the first enteral feeding connector is connected to the second enteral feeding connector and the connectors are attached to the respective enteral feeding tubes, a fluid passage is formed permitting fluid to flow from the second enteral feeding tube through the opening in the floor of the second enteral feeding connector around the receptacle and standoff and through the opening in the first enteral feeding connector to the first enteral feeding tube.

* * * * *